US008204580B2

(12) United States Patent
Kurzweil et al.

(10) Patent No.: US 8,204,580 B2
(45) Date of Patent: *Jun. 19, 2012

(54) USE OF PATTERNS IN PROCESSING ON MOBILE MONITORING DEVICE AND COMPUTER SYSTEM

(75) Inventors: Raymond C. Kurzweil, Newton, MA (US); Paul Albrecht, Bedford, MA (US); Lucy Gibson, Belmont, MA (US)

(73) Assignee: Kurzweil Technologies, Inc., Wellesley Hills, MA (US)

( * ) Notice: Subject to any disclaimer, the term of this patent is extended or adjusted under 35 U.S.C. 154(b) by 1473 days.

This patent is subject to a terminal disclaimer.

(21) Appl. No.: 11/136,338

(22) Filed: May 24, 2005

(65) Prior Publication Data
US 2006/0025697 A1 Feb. 2, 2006

Related U.S. Application Data

(60) Provisional application No. 60/574,268, filed on May 25, 2004.

(51) Int. Cl.
*A61B 5/0402* (2006.01)
(52) U.S. Cl. ...................................... 600/515
(58) Field of Classification Search .................. 600/509, 600/513, 515–520, 523; 607/27, 30, 59; 128/903, 904, 920, 923
See application file for complete search history.

(56) References Cited

U.S. PATENT DOCUMENTS

| 5,421,830 A * | 6/1995 | Epstein et al. | 607/30 |
|---|---|---|---|
| 5,544,661 A | 8/1996 | Davis et al. | |
| 5,966,692 A | 10/1999 | Langer et al. | |
| 6,073,046 A | 6/2000 | Patel et al. | |
| 6,261,230 B1 | 7/2001 | Bardy | |
| 6,270,457 B1 | 8/2001 | Bardy | |
| 6,280,380 B1 | 8/2001 | Bardy | |
| 6,364,834 B1 | 4/2002 | Reuss et al. | |
| 6,485,418 B2 | 11/2002 | Yasushi et al. | |
| 6,594,523 B1 * | 7/2003 | Levine | 607/30 |
| 6,609,023 B1 | 8/2003 | Fischell et al. | |
| 2001/0021801 A1 | 9/2001 | Bardy | |
| 2001/0039372 A1 | 11/2001 | Yasushi et al. | |
| 2002/0013517 A1 | 1/2002 | West et al. | |
| 2002/0013518 A1 | 1/2002 | West et al. | |
| 2002/0013613 A1 | 1/2002 | Haller et al. | |
| 2002/0052539 A1 | 5/2002 | Haller et al. | |
| 2002/0082665 A1 | 6/2002 | Haller et al. | |
| 2006/0025696 A1 * | 2/2006 | Kurzweil et al. | 600/509 |

OTHER PUBLICATIONS

Cardiac Surveillance at home, EP Lab digest Jan. 20, 2004.
Spacelabs Medical Receives FDA Approval for New Wireless, Multi-Parameter Waveform Clinical Messenger Jan. 19, 2000.
Remote Health-Monitoring System; Circuit Cellar magazine Jun. 2003.
An Ultra-low Power, Self-organizing Wireless Network and Its Applications to Noninvasive Biomedical Instrumentation 2002 IEEE/Sarnoff Symposium on Advances in Wired and Wireless Communications West Trenton, NJ, USA, Mar. 13, 2002.
Medical Intelligence—A Quebec firm invents the VPS, a revolutionary wireless portable automatic cardiac alert system Nov. 12, 2003.

* cited by examiner

*Primary Examiner* — Kennedy Schaetzle
(74) *Attorney, Agent, or Firm* — Fish & Richardson P.C.

(57) ABSTRACT

A system include circuitry to receive information from a mobile device including ECG data representative of a beating heart, circuitry to analyze the ECG data using at least one pattern to detect a notable finding in the ECG data and circuitry to determine at least one pattern to send to the mobile device, based on the analysis of the ECG data. The system sends the at least one determined pattern to the mobile device.

25 Claims, 5 Drawing Sheets

USE OF PATTERNS IN PROCESSING ON MOBILE MONITORING DEVICE AND COMPUTER SYSTEM

This application claims priority to and incorporates by reference in its entirety, U.S. Provisional Patent Application No. 60/574,268, filed May 25, 2004 and entitled "WIRELESS ECG MOBILE DEVICE THAT COMMUNICATES WITH A BASE STATION"

BACKGROUND

This invention relates to systems that monitor physiological characteristics of ambulatory patients.

In "Holter monitoring," a patient module acquires and records ECG data but does not analyze the data. After recording is complete, data is transferred from the patient module to a base station that analyzes the data. The base station identifies clinically notable findings for review by clinical specialists. In "event monitoring" data selection is performed in the patient module, either as the result of ECG analysis or due to a patient-initiated trigger. Selected ECG results are transmitted or downloaded to a system at a central facility.

U.S. Pat. No. 6,694,177 B2 by Eggers et al. entitled "CONTROL OF DATA TRANSMISSION BETWEEN A REMOTE MONITORING UNIT AND A CENTRAL UNIT" describes bidirectional communications between a remote monitoring unit and a central unit. The remote monitoring unit obtains a monitored data set from the patient, analyzes the monitored data set to obtain a derived data set and determines from the derived data set that communication with the central unit is required. The central unit analyzes the initially transmitted data set and instructs the remote monitoring unit to transmit an additional data set related to the monitored data set and a time when to transmit the additional transmitted data set.

SUMMARY

According to an aspect of the present invention, a system includes circuitry to receive information from a mobile device including ECG data representative of a beating heart, circuitry to analyze the ECG data using at least one pattern to detect a notable finding in the ECG data, circuitry to determine at least one pattern to send to the mobile device, based on the analysis of the ECG data, and circuitry to send the at least one determined pattern to the mobile device.

The follow are within the scope of the claim. The determined pattern includes the parameters of a mathematical model. The determined pattern includes a template derived from historical ECG data. The circuitry to analyze the ECG data includes circuitry to compare the analyzed ECG data to templates from categories of cardiac events in order to classify the ECG data. The determined pattern includes sending software. The pattern is a cardiac rhythm pattern. The cardiac rhythm pattern is a "bigeminy" rhythm that has alternating normal "N" and ventricular "V" beats, the pattern including a rhythm template that represents the "bigeminy" pattern as eight (8) beats of (N V N V N V N V) and wherein incoming beats are compared to the "bigeminy" template to determine if a "bigeminy" condition exists in signals of the incoming beats. The pattern is selected based on information from the mobile device, including user characteristics or physiological data samples collected for the user from the mobile device, or data derived by the mobile device from the physiological data samples, including heart beat patterns and heart rhythm patterns. The pattern is selected based on user characteristics, including patient clinical and demographic information, and is sent to initialize the mobile device. The pattern is new or updated software for execution by the mobile device. The pattern is a rule that has a set of conditions and an action to perform if the set of conditions is met. The rule is a classification rule. The rule is a processing rule. The set of rules is generated for a specific condition or patient.

According to an additional aspect of the invention, an arrangement includes a mobile device for processing ECG data representative of a beating heart, using at least one pattern to detect a notable finding in the ECG data, sending the ECG data corresponding to the notable finding to a second system and the second system executing a process for analyzing the ECG data corresponding to the notable finding and determining at least one new pattern to send to the mobile device, based on the analysis of the ECG data. The arrangement also includes a process to send the at least one determined pattern to the mobile device.

According to an additional aspect of the invention, a method includes receiving information from a mobile device including ECG data representative of a beating heart, analyzing the ECG data using at least one pattern to detect a notable finding in the ECG data, determining at least one pattern to send to the mobile device based on analyzing the ECG data, and sending the at least one determined pattern to the mobile device.

A pattern is a specification of characteristics, i.e., a form or model that is used by the mobile device and the second computer system to compare to incoming ECG data. In some cases, a pattern can include new or updated software for execution by the mobile device. Patterns can be represented as events in time. A pattern can be any specification of characteristics or a set of parameters. A pattern can be a rule that has a set of conditions and an action that is to be performed if the set of conditions is met. Patterns are used to affect subsequent processing by the mobile device. Thus, the second computer system modifies operation of the mobile device by changing new or revised patterns.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
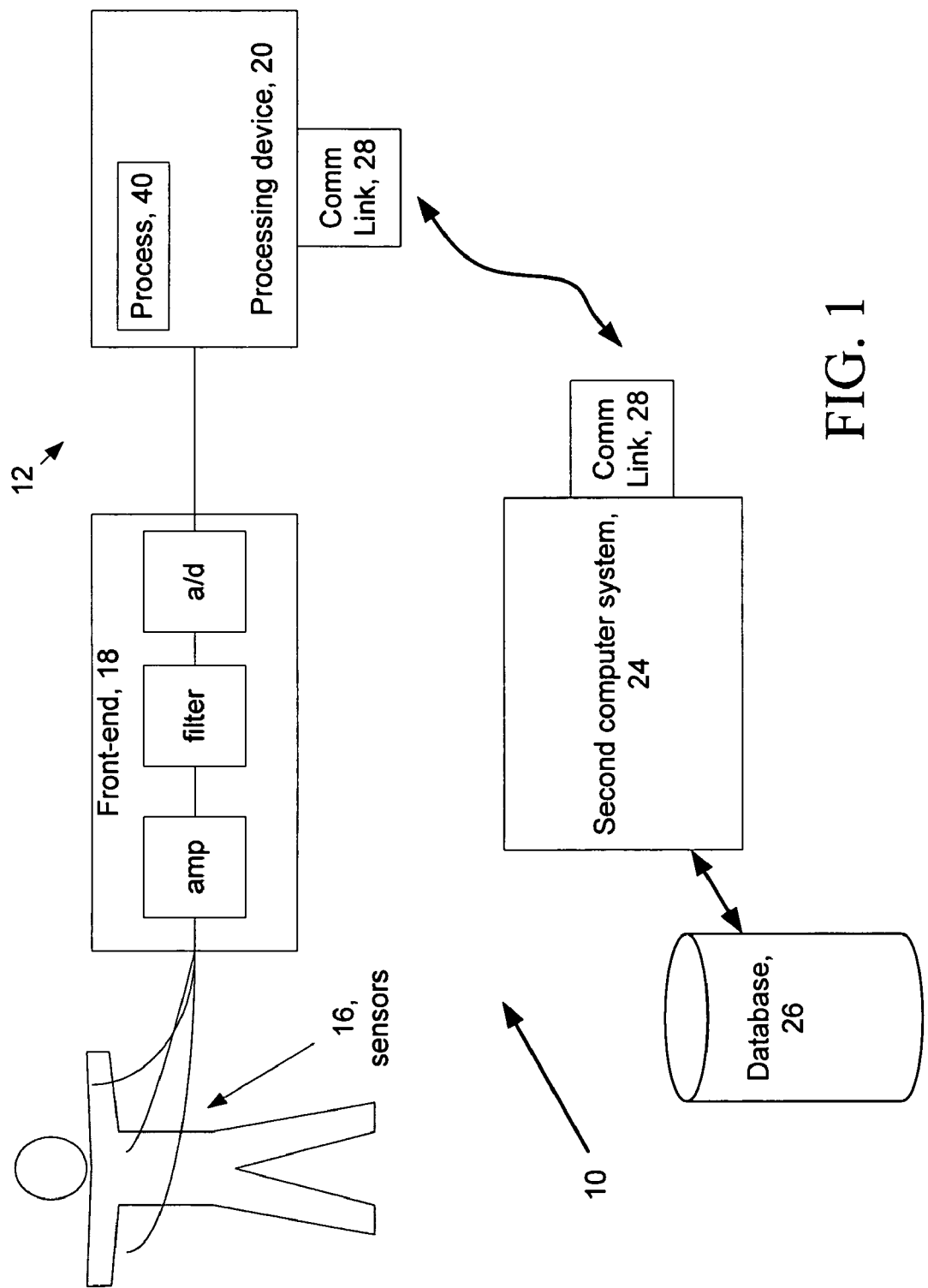
FIG. 1 is a block diagram of a system for patient monitoring and analysis.

Referring to FIG. 1, a system arrangement 10 includes physiological sensors 16 connected to a mobile patient device 12 that collects, processes, and records findings from physiological data provided from the sensors 16. The mobile patient device 12 includes a mobile processing device 20 that executes a process 40 that determines notable findings in real time and sends the notable findings over a communication link 28 to a second computer system 24, which has computing resources that allow it to reprocess the physiological data corresponding to the notable findings with greater accuracy than the mobile device 12. The second computer system 24 can produce a report and send the results for clinical review (not shown).

The second computer system 24 analyzes differences between the results from the mobile device 12 and the results from the reprocessing by the second computer system 24, and may generate or retrieve new "patterns" (discussed below) to improve processing on the mobile device 12. The new patterns are sent over the communications link 28 to the mobile device 12. The second system 24 works cooperatively with the mobile device 12 to provide the high quality and timely detection of notable findings.

The sensors 16 are attached to the body of the patient (or may be embedded in clothing next to the skin). The sensors 16 provide physiological signals to a front-end 18 of the mobile device that typically includes one or more amplifiers, one or more filters, and one or more A/D converters. The mobile device 12 is typically worn or carried on the body of the patient. The front end 18 amplifies and filters the analog signals and converts the analog signals to digital data for processing by a processing device 20 in the mobile device 12. The system arrangement 10 can be implemented in several different configurations as discussed below.

Communications between the second computer system 24 and mobile device 12 is bi-directional. The mobile device 12 records, analyzes and/or reports on patient data, such as electro-cardiograph (ECG), blood pressure, respiration, temperature, EEG (brain waves), Electromyography, etc. In one embodiment, the mobile device 12 is configured to detect cardiac abnormalities in an ECG signal.

The second computer system 24 may maintain a large database 26 of physiologic patterns. The database 26 stores patterns, reference templates, and parameters for use in beat and rhythm classification by the mobile device 12 or second computer system 24. The second computer system 24 maintains historical reference data on the subject, including ECG strips, templates and reference data for future processing.

Initialization software to enable the mobile device 12 to communicate with the second computer system 24 is downloaded to the mobile device 12. The second computer system 24 configures the mobile device 12, and provides software, parameters and reference data for use by the mobile device 12. The installation can take into consideration existing hardware and software configurations of the mobile device 12. The initial download can be for instance a "Setup.exe" type application that selects and manages download of other components in the downloaded software. The second computer system can also transmit software updates to the mobile device.

Figure 2:
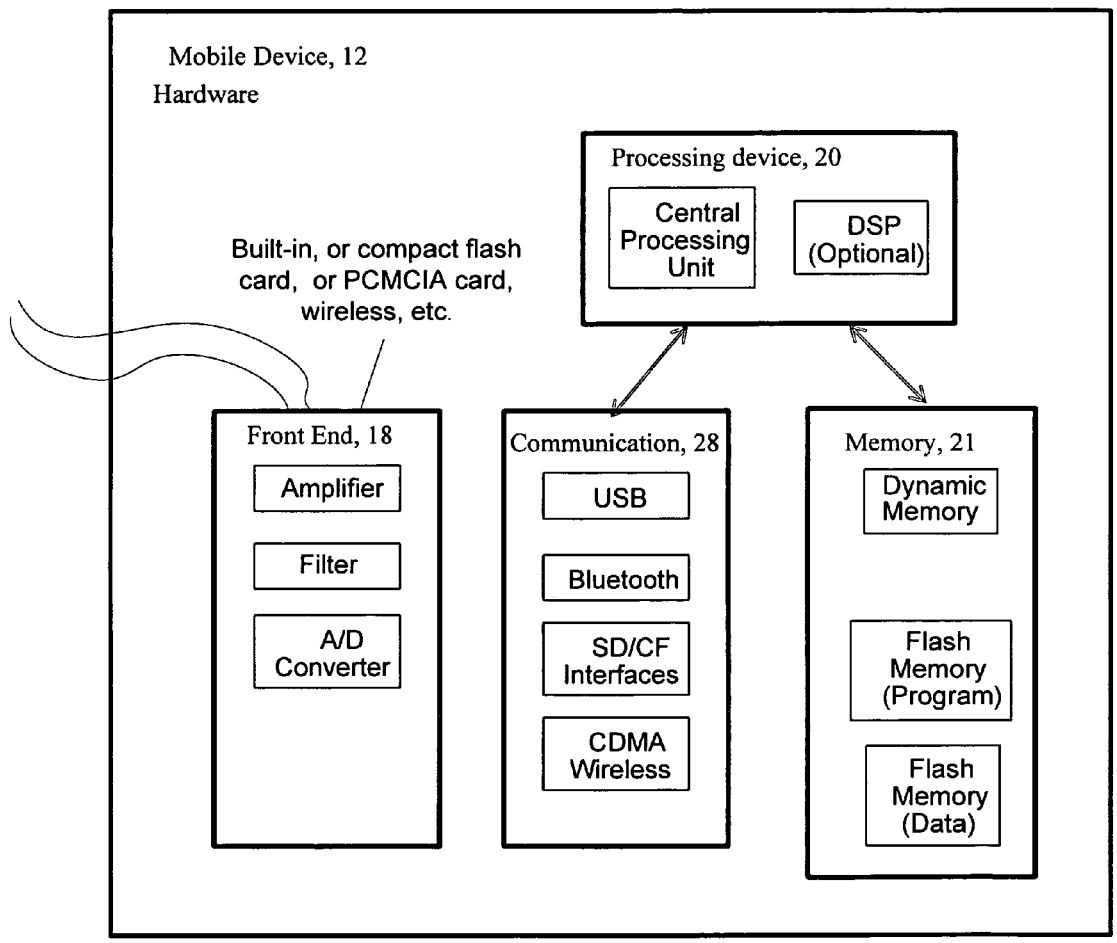
FIG. 2 is a block diagram of a mobile device.

Referring to FIG. 2, the mobile patient device 12 includes three functional components, as shown: a front end 18 that conditions and digitizes signals sensed from mobile device of a patient; a processing device 20 and associated support hardware to produce a computing device that processes the signals based on software and algorithms; and a communications path 28 such as a wireless link that allows the processor to communicate with the second computer system. The components may be grouped into a single device or may be configured as two or three separate devices. A patient wears electrode sensors (FIG. 1) that are attached to a lightweight patient cable assembly (not numbered). The other end of the cable is attached to a compact card which can plug into a standard type slot, such as a compact flash slot or PCMCIA slot, on a computer.

In one configuration, the card includes input processing circuits (front end 18) to amplify, filter and digitize the input signals from the electrode sensors, and non-volatile flash memory 21 to store the ECG and other data. The card plugs into a standard slot on the processing device 20, e.g., a PDA or handheld PC, which does the processing and communicates with the second computer system 24, over established wireless networks. In another configuration, (not shown) the patient wears a garment with built in sensors and a built-in front end 18 (e.g., amplifiers, filters, and analog to digital converters), i.e., integrated ECG sensors that will permit less intrusive monitoring than conventional stick-on electrodes. The garment-based sensors have a known and predictable electrode configuration. Garments with ECG sensors may have an associated identifier that specifies the ECG sensor and lead configuration. The configuration identifier may be encoded into the garment to allow it to be automatically determined by the patient module or base station. The identifier may use an encoding technology such as RFID or an electrically accessed circuit incorporated into the garment. Once the identifier is known, the mobile device 12 and the second system 24 may adapt the processing to the sensor configuration corresponding to the identifier.

In another configuration, the front-end 18 communicates with a mobile phone/computer that is powered by a long life battery or fuel cell. The mobile phone/computer has a standard mobile operating system on it that allows the patient to run standard applications. The mobile phone/computer can be initialized for the patient mobile device function by downloading an application that configures the mobile phone/computer so that it can communicate with the front end and communicate over the wireless mesh or Internet.

Front End

The front end 18 interfaces to the physiologic sensors and makes available a stream of digital data. The sensors to which the front end 18 connects may include conventional sensors, such as ECG electrodes or advanced technology, such as a garment that incorporate the sensors into the fabric, as discussed above. For garment-based sensors, the front end may also be incorporated into the garment. The front end can be separate from the mobile computer or the front end 18 may communicate with the mobile computer by wire or by a wireless connection such as Bluetooth. The front end can receive power from the mobile processor over a wire. The front end, when connected wirelessly, may save power and transmission costs by storing signals and then regularly transmitting the stored signals during a brief transmission interval. The front end may include memory to store digitized signals.

Mobile Processing Device

The mobile processing device 20 analyzes the signals and communicates with the second computer system through the wireless link. The mobile processing device is coupled to the front end 18. The mobile device 12 includes memory 21, including non-volatile memory, such as flash memory that stores the programs that run in the device and the digitized signals. The mobile processing device 20 and second computer system 24 may use a secure communication protocol, or encrypt data exchanged between the mobile computer and second computer system 24. The mobile processing device 20 and second computer system 24 may use efficient data streaming protocols to minimize network traffic, instead of protocols such as TCP/IP. The mobile processing device 20 may be a PDA or a wireless phone. The mobile processing device 20 may be or include a specialized processor to optimize signal-processing capabilities of the mobile device 12, such as a digital signal processor unit. The mobile processing device 20 provides a user interface through which the user can interact with the mobile device, e.g., the mobile computer may be accessible using a browser. The user may review settings and modify operation of the mobile device.

Communication Path

The communications path 28, such as a wireless link, provides bi-directional connectivity to allow the mobile device 12 to function as a networked computer. The wireless link 28 may use the Internet to communicate with the second computer system 24 or a wireless mesh to communicate to the second computer system 24. The wireless link may be integrated as part of a mobile phone or PDA.

The mobile device records, analyzes and reports on spatial parameters such as the patient's motion, physical orientation and location as determined by global positioning systems (not shown but would be common in cell phone, for instance) in the device. The mobile device uses the spatial parameters to determine whether a change in physiological data can be attributed to a change in physical orientation of the patient. The mobile device may use the signals from motion and physical orientation to detect that a patient has fallen down. The mobile device is configured to report that event to the mobile device facility immediately. Prior to reporting, the mobile device gives the patient time to prevent the report, and prompts the patient with a cue (e.g. sound, vibration) that if responded to, cancels the report.

The mobile device 12 may allow the patient to mark an occurrence of a symptom, including onset/offset, or to document activity. The mobile device may allow the patient to add a voice note to each mark, or to produce a mark by adding a voice note. The mobile device is used by the patient to manually trigger a request for help. When reporting a potential emergency, the mobile device may communicate directly with a facility or system other than the second computer system.

Patterns

A pattern as used herein is a specification of characteristics, i.e., a form or model that is used by the mobile device 12 and the second computer system 24 to compare to incoming ECG data. In some cases, a pattern can include new or updated software for execution by the mobile device 12. An exemplary pattern involving a model and specification of characteristics is the pattern of a single heart beat, e.g., a "heart beat pattern."

The "heart beat pattern" is represented by QRS samples of the signal, where each sample is represented according to amplitude (relative to a reference level) and time of occurrence of a point in the pattern (relative to some point in the beat). For example, if the time of the Q peak is considered time zero, then the time for R is the time from Q to R. These relative measures allow the "heart beat pattern" to be compared to newly detected beats, to detect clinically significant episodes or events.

The heart beat pattern and other parameters, such as the beat width, make up a "beat template," which may be derived from a number of similar beats. A "beat template" is produced for each beat category (e.g., normal, ventricular, etc.). Newly detected beats are compared to the beat templates from each beat category in order to classify the beats. Comparing a beat to a beat template is a type of pattern matching.

Another type of pattern matching can be used for cardiac rhythm detection. The rhythm called "bigeminy" has alternating normal "N" and ventricular "V" beats (N V N V ... ). A rhythm template may represent "bigeminy" as eight (8) beats: (N V N V N V N V). Incoming beats are compared to the "bigeminy" template to see if a "bigeminy" condition exists in the incoming beats.

Patterns can be represented as events in time, such as the QRS waveform or the pattern of beats described above. However, a pattern does not have to be described according to time. A pattern can be any specification of characteristics or a set of parameters. For example, an RR interval can classified according to the "pattern" of its length. To perform pattern matching and classification of a signal, pattern matching criteria are defined. Thus, in the above rhythm example, a beat is classified as being either N (normal), V (ventricular), or possibly something else like fusion (in which case it would not match the given "bigeminy" rhythm).

Another type of pattern is a rule. A rule has a set of conditions and an action that is to be performed if the set of conditions is met. For example, a beat classification rule may be: "if a beat is wide, classify it as ventricular." The condition is "wide beat," and the action is to "classify beat as ventricular." This is an example of a classification rule. Other types of rules include processing rules, for example, a rule to determine when to escalate a cardiac finding on the mobile device 12 and immediately notify the second system 24. A set of rules is generated, e.g., by the second system for a specific condition or patient. At least a subset of those rules is downloaded to the mobile device 12 for a specific condition or patient. The rules affect subsequent processing by the mobile device 12.

Figure 3:
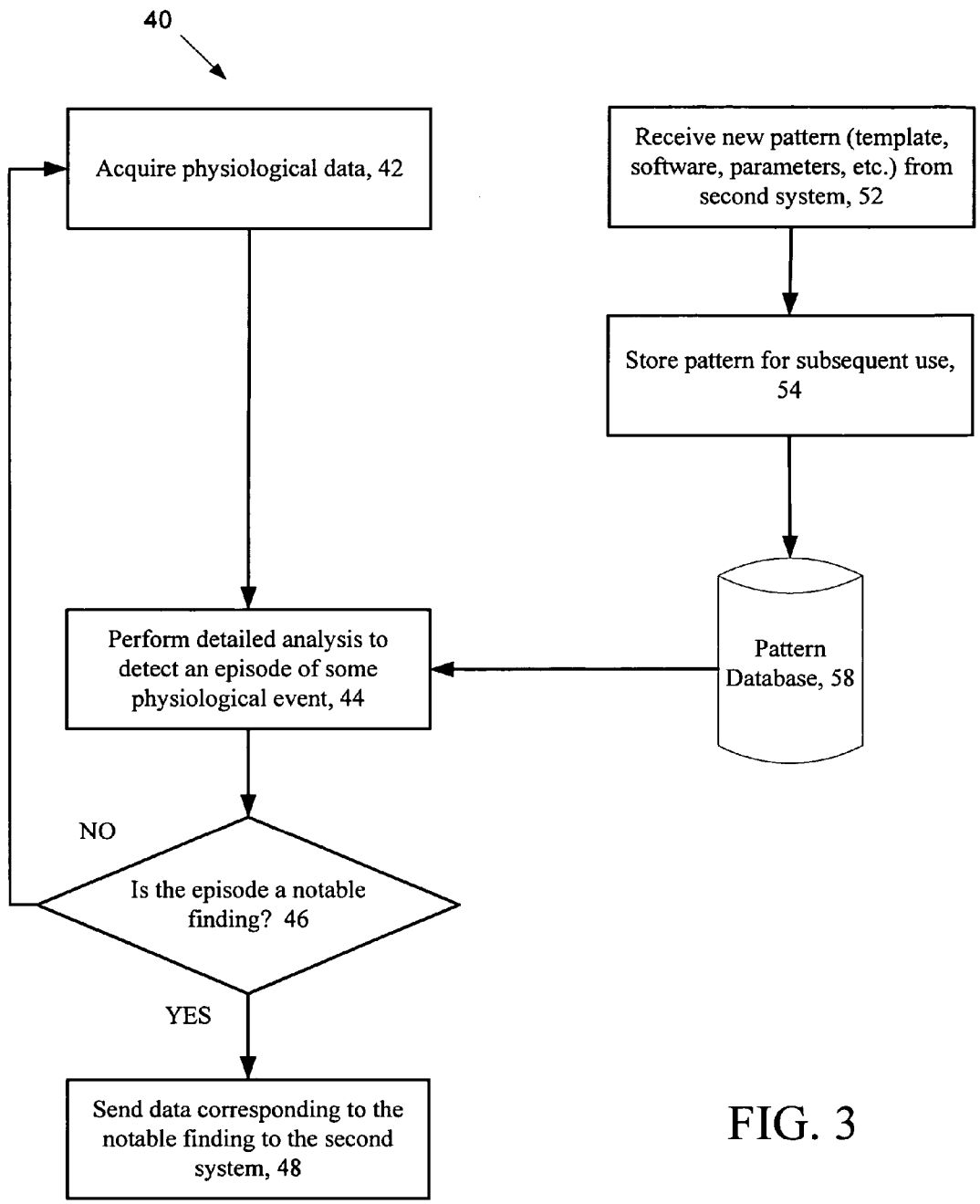
FIG. 3 is a flow chart detailing aspects of cooperative processing on a mobile device.

Referring to FIG. 3, a cooperative processing process 40 that occurs on the mobile device 20 is shown. The mobile device (FIG. 1) acquires 42 physiological data from the frontend 18. The process 40 performs a detailed analysis 44 of the data to detect an episode of some physiological event. If an episode was detected, the process 40 determines 46 if the episode can be considered as a notable finding. Examples of notable findings include: an episode which has been classified as a clinically important finding (such as atrial fibrillation); or an episode that contains too much noise for the mobile device to successfully analyze; or a pattern that does not fit any of the templates in the mobile device. If the episode is not a notable finding, the process 40 begins again. If the episode is considered a notable finding, the process 40 sends 48 the physiological data corresponding to the notable finding to the second system 24. The physiological data is sent 48 either immediately after the notable finding was determined, or multiple notable findings may be stored and sent periodically.

For example, if the device 20 is to detect heart arrhythmias, then the physiological data is ECG, and the detailed analysis 44 would be a cardiac arrhythmia detector. Notable findings for cardiac arrhythmias include ventricular flutter, ventricular fibrillation, atrial fibrillation, etc. If a detected arrhythmia is determined to be a notable finding, because it has been classified as, for example, atrial fibrillation, then the ECG corresponding to the episode of atrial fibrillation (i.e. 2 minutes of ECG) is sent 48 to the second system 24. If the episode of atrial fibrillation was 25 beats long, then a segment of ECG 2 minutes long that includes the 25 beats could be sent 48, along with an indication of the onset and offset of atrial fibrillation within the selected ECG.

The data corresponding to the notable finding, sent in 48, can be data generated by different parts of the process 40. The example describes sending the ECG, which is the raw physiological data that was input to the process 40. The input data is sent so that the second system 24 can reprocess the same data with its better resources. The process 40 may also send intermediate or final results of its analysis of the data, so that the second system 24 can improve the processing of the process 40, as follows.

The detailed analysis 44 detects episodes of events using patterns, which could be beat templates, rhythm templates, rules, etc., as described above. These patterns are stored on the processing device 20 in the pattern database 58. New patterns are received 52 on the mobile device 20 from the second system 24. The new patterns are stored 54 in the pattern database 58, to be used by the detailed analysis 44.

Figure 4:
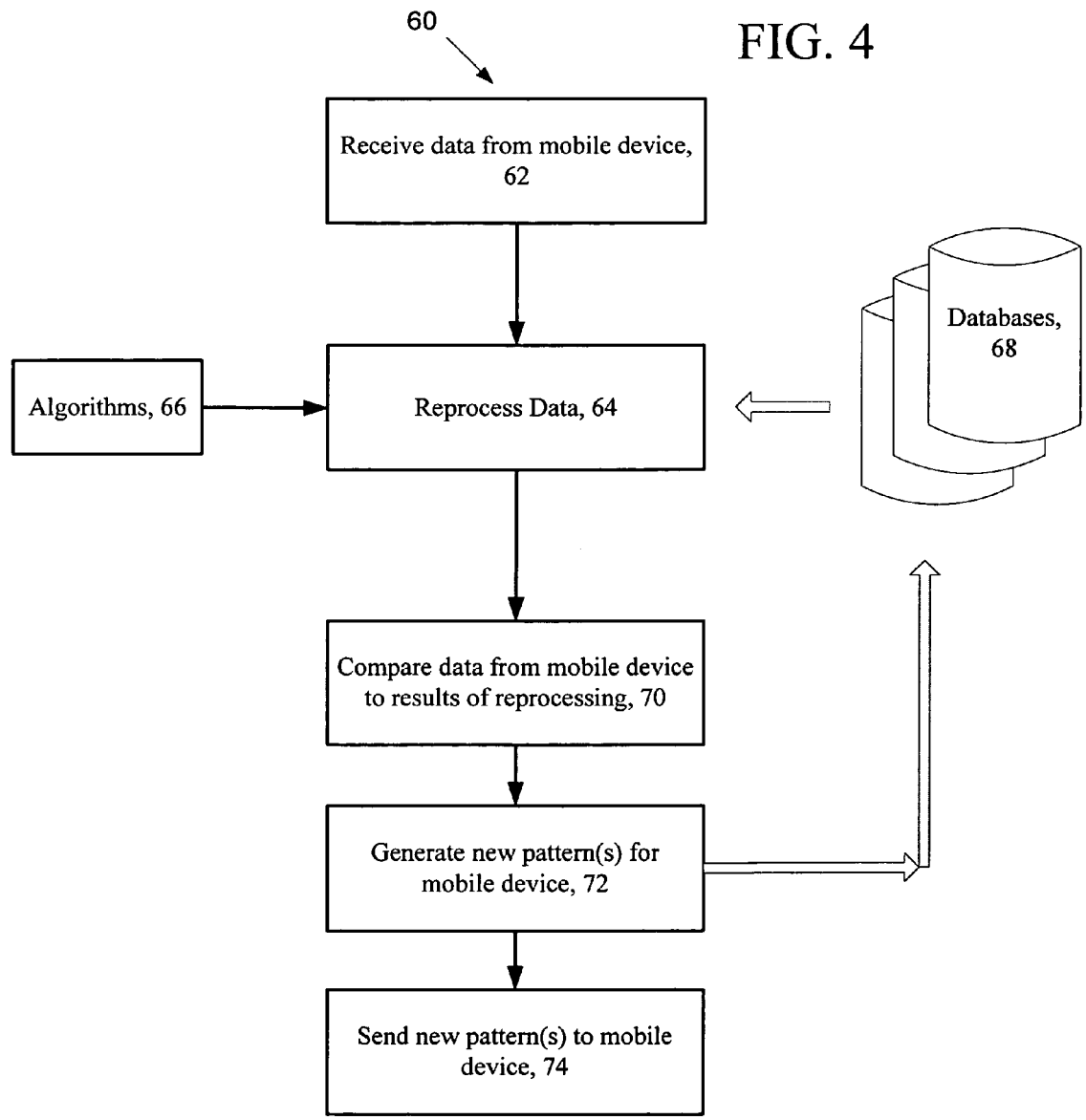
FIG. 4 is flow chart detailing aspects of cooperative processing on a second system.

Referring to FIG. 4 cooperative processing 60 that occurs on the second system 24 is shown. The process 60 receives data 62 from the mobile device 20, e.g., the raw physiological data input to the mobile device 20. In addition, the data may include intermediate or final results of analysis on the mobile device 12. The data is reprocessed 64 using more extensive resources than are available on the mobile device 12, including a variety of algorithms 66, more powerful processors (not shown), and a larger set of databases 68. The reprocessed data is compared 70 to the data received from the mobile device 12. If there are no significant differences, then the mobile device 12 is not updated.

If significant differences are found, then the reprocessed results on the second computer system are assumed more accurate, and those results are used to generate 72 new patterns for the mobile device 12. The new patterns are used to improve processing on the mobile device, e.g., (to make processing more accurate, more efficient; reduce communication time with the second computer system, etc.). The new patterns are sent 74 to the mobile device 20, and are stored in the databases 68, along with any relevant data, such as the raw physiological data received from the mobile device 12.

As an example of the type of processing, assume again that the system 10 is a cardiac arrhythmia detector. The data received 62 from the mobile device could be ECG data as well as an indication of the onset and offset of the particular arrhythmia. Suppose the mobile device sends 2 minutes of ECG data with an indication of 25 beats of atrial fibrillation, and the reprocessing 64, also detects atrial fibrillation, but for a period of 10 beats. The comparison 70 would show a significant difference, and a new pattern would be generated 72 and sent 74 to the mobile device 20.

The databases 68 store data for the specific patient wearing the portable device, and data that were compiled from many patients. The databases may contain physiological data, derived data, rules, procedures, programs, templates, etc.

If the second system detects a notable finding from the data sent by the mobile device 12, it may perform several actions (not shown) in addition to generating new patterns, including notifying clinical personnel and/or the patient of determined clinically notable findings. Some notifications may be low priority, and may be carried out in the form of daily updates to clinical personnel for review. If the second system 24 detects a more serious finding, the second system 24 could make the notification immediately, and contact a physician or emergency services directly instead of the clinical review personnel.

The process 60 may include sending a new pattern to modify the mobile device's processing. Based on the analysis of the data, the second computer system directs the mobile device to send additional data or to modify the operation of the mobile device by changing what the mobile device looks for, or to improve the processing by providing more appropriate reference data, processing rules or new or revised patterns of other kinds.

Thus, processing workload is split between the mobile device 12 and second computer system 24. The balance is adjusted to suit available mobile technology. The mobile processor 20 in some aspects is a pre-processor for the second computer system 24. The mobile device 12 receives operating parameters and reference data for algorithms executed on the mobile device 12, as well as executable code from the second computer system 24. The mobile device 12 operates in standalone mode when access to the second computer system 24 is not available. During that time, the mobile device 12 saves notable findings and information in non-volatile memory. In typical operation, the mobile device 12 periodically rather that constantly communicates data to the second computer system 24. That is, the mobile device sends periodic updates of information to the second computer system 24. Immediate contact with the second computer system occurs only if there is a potentially serious event, or an event that needs the additional processing resources of the second computer system, rather than a notable finding.

Under normal operating conditions, the second computer system 24 may be in regular contact with the mobile device 12. Even when the mobile device 12 does not detect any findings that herald a possible problem, the mobile device 12 may send (or be asked to send) data. The data are analyzed by the second computer system 24, which has access to greater computational and database resources than the mobile device. If the second computer system 24 finds errors, it can send the mobile device 12 additional reference data and parameters to correct the processing, as discussed above. The intervals between data transmission can be controlled by the second computer system 24, and can take into account the clinical risk of the patient or the complexity of the signals being processed by the mobile device 12.

During cooperative processing, the selection of findings to look for and the threshold for detecting clinically notable findings are governed and modified, as needed, by the second computer system 24. The second computer system 24 conducts a detailed and thorough analysis that uses, for example, state of the art ECG analysis of the signals to determine whether the data includes a notable finding. A final examination and classification of the data is performed by the second computer system 24. The second computer system 24 determines a new pattern to send to the mobile device 12, based on the analysis, and sends the new pattern to the mobile device 12.

The mobile device 12 and second computer system 24 work cooperatively and collaboratively as a hybrid of distributed processing. Cooperative processing attempts to strike a balance between the processing requirements on the mobile device 12 and the amount of data that is sent to the second computer system 24 vs. the need to perform high quality analysis.

Cooperative processing in the context of ECG analysis is a hybrid between so called "Holter monitoring" and "event monitoring." In "Holter monitoring," a patient module acquires the ECG data but does not analyze the data. After recording is complete, the data are analyzed at a base station. The base station identifies clinically notable findings for review by clinical specialists. In "event monitoring" data selection is performed in the patient module, either as the result of ECG analysis or due to a patient-initiated trigger. The selected ECG results are transmitted or downloaded to a system at a central facility. In contrast, in cooperative processing, both the mobile device 12 and the second computer system 24 play a role in processing acquired data, and as discussed either can raise an alert to the patient or send a notification to a central facility.

Clinical Performance

The role of the mobile device 12 is to have relatively good sensitivity to potential events and not be too susceptible to false negatives; whereas the role of the second computer system 24 is to improve the positive prediction capabilities of the system 10 by rejecting false positives, without decreasing the sensitivity of the system 10 by rejecting true positives.

Configurability

The system arrangement 10 is configurable so that medical personnel can determine what types of episodes will be reported. The thresholds for reporting can be set low for a new patient, so that almost any abnormality will be reported. For patients with known abnormalities, the thresholds can be set to report and send the ECG data only when the abnormality is more severe than prior episodes of the same abnormality.

Reference Data

The second computer system 24 sends reference population data and parameters to the mobile device 12 as the cooperative processing executes in the mobile device 12 to make decisions as it processes the incoming ECG data. The reference data and parameters are sent at the start of monitoring or at any point during the monitoring.

The reference data includes some or all of the following information:

Parameters such as probabilities, rates, interval durations and amplitudes;

Templates of individual beat morphologies, as discussed below and sequences of beat types (such as the bigeminy pattern discussed above).

The reference data is indexed according to characteristics, such as age, gender, height or weight. The second computer system may take into consideration the patient's characteristics when selecting the reference data. The reference ECG data may also be indexed according to the ECG lead configuration. If the patient's lead configuration is known, the second computer system may select or modify the reference ECG data to be more appropriate to specific sensor configuration. The reference data is tailored to the specific patient and specific sensor configuration, in order to improve analysis by the patient mobile device 12.

The reference population data is used in processing by the second computer system, as described below. The data includes data related to patient-specific learning based on past monitoring sessions. For example, if a patient has had an intermittent bundle branch block, a template and characterization of the bundle branch block beat could be created by the system 10, and bundle branch block could be more confidently detected if it occurred during a new monitoring session.

Having a set of previously observed ECG patterns makes it easier to detect new patterns. For example, if a patient previously had bundle branch block, but there is a change in the extent of the block causing a significantly wider beat morphology, the change is detected.

When the mobile patient device detects a new beat type or an abnormality that is not already represented in its memory, the module may send the data to the second computer system 24. This allows the second computer system to maintain a complete record of known ECG findings for the patient.

As with the population data, the patient-specific data may be indexed for the sensor configuration. The reference patient data as with the reference population data is used by the second computer system 24 in processing the data from the mobile device 12, as described below.

Conditions for In-Depth Analysis

Generally, the mobile device 12 captures data from the patient and processes the data. The mobile device sends the data to the second computer system 24 for processing under certain conditions. The mobile device sends the data to the second computer system 24, when the mobile device 12 encounters an ECG pattern that has not been seen before or that has been seen infrequently. The mobile device 12 sends the data to the second computer system 24 when the mobile device encounters a transition to a new rhythm. For example, whenever the mobile device 12 detects an ECG patterns that seems like atrial fibrillation, the mobile device 12 transfers a segment of the ECG data containing the onset of the detected pattern to the second computer system 24 for detailed analysis to determine if the segment fits the pattern of atrial fibrillation and, if it does, to determine the exact onset of the atrial fibrillation. The analysis performed by the second computer system 24 would likely involve detailed processing of the ECG to remove the effect of the QRST complex and to analyze the atrial activity.

Other conditions under which the mobile device 12 sends data to the second computer system 24 include when the mobile device 12 falls behind making a determination on a segment of ECG data. The mobile device 12 also sends data to the second computer system for trending or audit purposes at periodic intervals or at pre-specified times or conditions.

Cooperative process allows for contrasting and comparing mobile device and second system results. The second computer system 24 is likely to have greater processing power than a mobile device 12, and thus the second computer system is better suited for in-depth analysis involving computationally intensive pattern recognition. The analysis performed on the second computer system 24 can compare the ECG against a large database of ECG records and patterns. The database can include the patient's past ECG data and population data. This combination of greater power and larger available reference data permits the second computer system 24 to perform rigorous in-depth analysis of the ECG to confirm findings, find new patterns and reject errors. The more powerful computing resources on the second system allow faster processing than in the mobile device, and less ECG data has to be processed on the second system because the mobile device only sends a portion of all its findings to the second system.

Even though mobile processors are increasingly powerful, in-depth analysis by the mobile device 12 with existing processors would draw significant power. The mobile device 12 would require larger batteries or more frequent re-charging, both of which would make the mobile device 12 more cumbersome to use. For the near-term, there is a practical limitation on how much of the processing can be done by the mobile device 12. Likewise, existing wireless network capability, reliability and cost makes it prohibitive to stream all of the ECG data to the second computer system. Even if it were reasonable to do so, the economics of housing and supporting dedicated second computer systems 24 would probably be unfavorable, and would require a larger second computer system 24 than the cooperative processing approach. Furthermore, there would be an added cost because the real-time reliability of the second computer system 24 and network connections would need to be greater.

Even as technology progresses and mobile processors become more powerful and more power efficient, and fuel cell technology provides increased "battery" life, the cooperative processing approach will remain useful. One reason is convenience. Patients will want and expect devices to continue to shrink in size yet provide increasing functionality. Even though it may be possible in future years to do almost all of the ECG processing in a device that is the size of a present-day PDA, for instance, patients would likely not want to have devices that large. This will be especially true of those who are relatively healthy and are using the device for routine mobile monitoring as part of a general regimen of keeping healthy.

In a limited computing environment, the processing can be set to find representative events. An example is the problem of categorizing beat type templates under different body positions. Changes in body position (e.g. supine vs. upright) can cause a shift in the position of the heart, which usually changes the shape of the QRS complexes recorded by the different leads. A QRST template may be indexed by QRS electrical axis (or modified based on the QRS axis) so that two different QRST morphologies, which differ because the heart was in a different position, can be determined by the algorithm to be the same beat type.

Figure 5:
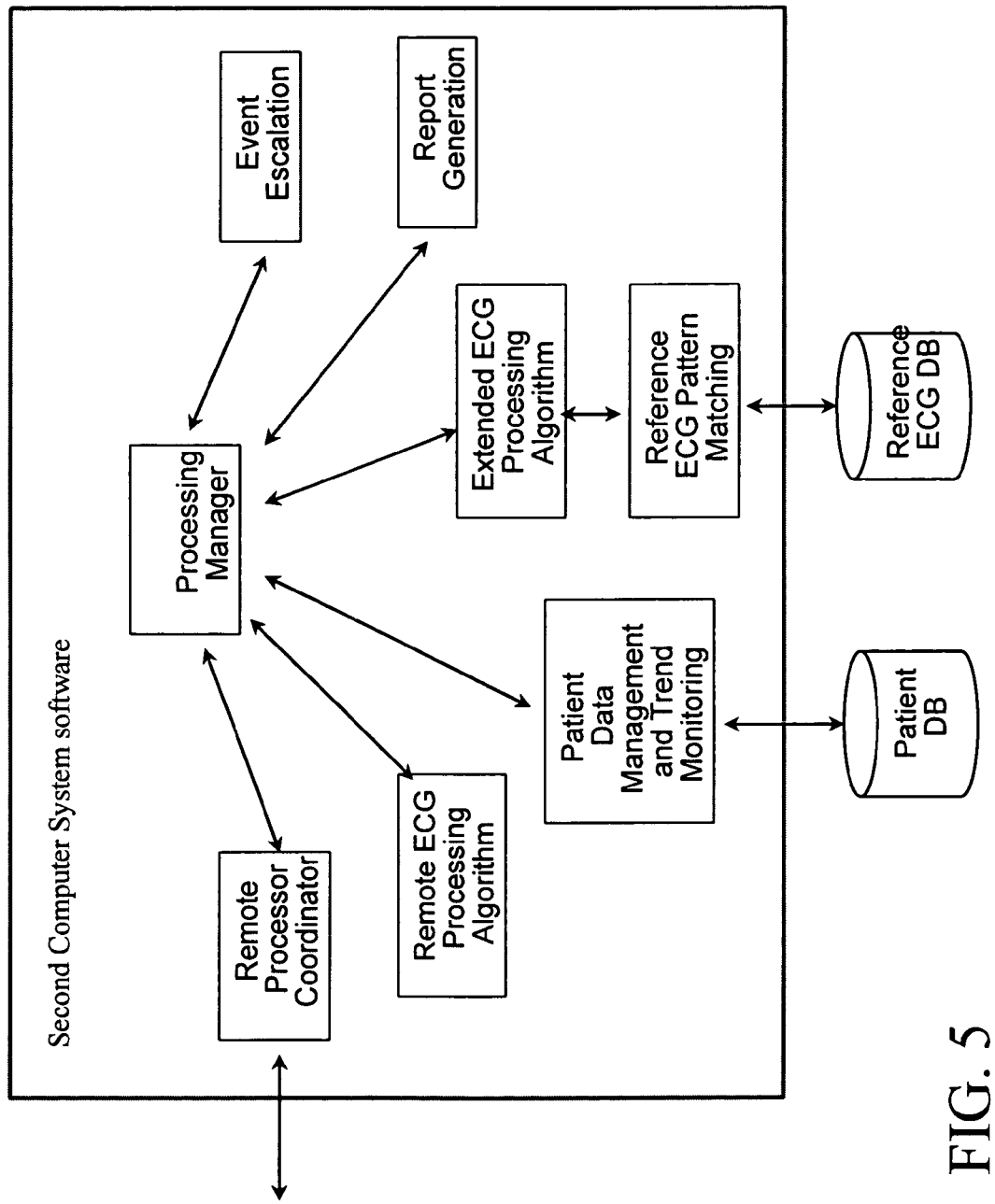
FIG. 5 is a block diagram of computing functions performed by the second computer system.

Referring to FIG. 5, the second computer system can operate by itself or part of a larger facility including a server-farm. The second computer system can be configured to include a processing manager, remote processor coordinator and remote ECG processing algorithm manager. In addition, the second computer system includes a patient data management and trend monitoring manager that interfaces with and manages the patient database. The second computer system includes an extended ECG processing algorithm and reference ECG Pattern Matching manager. The second system also includes processes for report generation and event escalation.

The second computer system 24 can be implemented in many different ways. For example, as a single computer system that is network enabled at a patient's home. Such a private second computer system may maintain a detailed record of ECG findings over time for the patient and can be configured to escalate specific types of findings by sending data to another second computer system at a clinical monitoring facility, or by generating a fax, e-mail, etc. to be sent to medical personnel. A single second computer system may capable of concurrently servicing more than one patient mobile device.

The second computer system 24 at a monitoring facility may be part of a large facility that can establish a session with the mobile device 12 so that the same server continues to interact with the mobile device 12. The second computer system at a monitoring facility may be configurable on a per-patient basis to specify escalation rules for different types of findings.

The second computer system 24 may receive the voice notes from the mobile device 12, discussed above. The second computer system uses speech to text technology to produce a text note from the speech note generated by the mobile device 12 to associate with the data. The second computer system software may pro-actively request the signals from the patient to develop a representative sampling of the ECG over time. The second computer system may interact with a database to keep a historical record of part or all of the data that it receives from the mobile device. The second computer system may analyze the historical ECG record to produce beat templates and rules relevant to the patient.

The second computer system 24 can have access to any of the data in the mobile device 12. In addition, the second computer system 24 sends as appropriate updated parameters that determine the general operation of the mobile device 12, including the types of episodes that are detected and reported. The second system sends corrections to internal classifications or to templates produced and held by mobile device 12. The second system sends reference data including ECG beat templates, historical data for the patient, e.g. what is normal for that patient. The second system sends instructions intended for the patient.

Templates

Exemplary templates can be generated for various functions and processing performed by the system. The templates can be adjusted and used by the mobile device and the second computer system based on findings observed during processing of the ECG signals.

Data Acquisition

A subject may wear ECG electrodes or an undergarment with integrated ECG sensors. For routine monitoring 1 or 2 channels of ECG, signals are usually acquired by the ECG module, which amplifies the ECG signal and filters it to preserve frequencies in the range of 0.05 to 100 Hz. The ECG signal is sampled typically at a frequency in the range of 250 to 360 Hz. The digitized ECG is transferred to the mobile processor for processing. The mobile processor saves the data in its flash memory.

Ventricular and Atrial Activity Processing

Ventricular processing involves:

Bandpass filtering of the ECG in a specified frequency range of e.g., (5-40 Hz) to emphasize the signal content of the QRST complex.

Multi-channel peak detection to identify candidate QRS complexes in the filtered signal.

Measurement of the subject's physical orientation to detect shift in body position.

Comparison of detected beats against templates derived from live ECG data and against reference templates provided by the second computer system.

If the subject's body position has changed, the comparison against the live ECG templates can consider the change in the QRS axis. The template can keep track of QRS shape as a function of the QRS axis.

Reference templates may include QRS axis information. The template matching may be restricted to templates that have a QRS axis similar to the current live ECG. Or the reference template may be transformed to make the QRST axis comparable with the live ECG data.

When a new QRS morphology is found, ECG preceding and following is sent by the mobile device to the second computer system for in-depth analysis. The second computer system can send back information that included templates or parameters that will be used in classification of QRS morphologies.

Atrial Activity Processing Involves:

Preliminary classification of the beat based on template matching

Multi-channel P-wave detection to look for individual P-waves preceding QRS complex.

For each P-wave, comparing it against templates derived from recent beats and against reference templates provided by the second computer system.

For each P-wave, producing a measure of its significance based on the template match and a signal to noise.

Additional processing (if single P-wave is not found and if the device is keeping up with real-time signals) involving:

Adaptively subtract the QRST complex by subtracting out the matching QRST template P-wave detection in the QRST interval to identify a P-wave.

Beat Classification

Beat classification determines whether a beat is of atrial, junctional or ventricular origin. The processing involves:

Producing timing and morphology measures of the beat

Measuring how well the measures of (P)QRST morphology and timing measures match predefined parameters sets.

Default parameters sets based on conventional clinical definitions of ECG analysis.

Customized parameter sets are supplied by the second computer system based on past ECG or based on other data obtained form the subject. These may replace or augment the default parameter sets.

Measuring the correlation of an observed (P)QRST to (P)QRST templates. The measures include the following:

Similarity of the QRST to an existing QRST template cluster that is either derived from the live ECG data or provided by the second computer system based on prior ECGs.

Similarity of the P-wave (if one has been detected) to an existing P-wave template cluster and whether that template is associated with the QRST cluster.

Whether the (P)QRST template cluster has been definitively classified as atrial, junctional or ventricular origin Measuring how well a (P)QRST for the most recent N beats matches previously observed patterns for N beats.

The matching includes absolute and heart-rate-normalized timing intervals of the QRS complexes and P-waves, along with the clustering measures of the QRS complexes and P-waves.

The number (N) of beats compared ranges from 2 to 8 or more based on how well the processing is able to keep up with the real-time signals.

The second computer system can provide the mobile processor with previously classified multi-beat patterns to use as reference data. The mobile processor limits the number of patterns compared based on the available processing time.

Updating of templates based on the classification to include the contribution of QRS complexes put into the template cluster. Clusters can be produced, merged or classified based on rules in the mobile processing algorithm or based on information sent by the second computer system.

Producing an audit trail that can be used (if necessary) by the second computer system to review the decisions made by the mobile processor.

Rhythm Classification

Rhythm classification involves looking for clinically recognized rhythm patterns in a sequence of beats. Multiple rhythm classifications may be determined for a set of beats, each classification having an associated confidence measure and clinical severity.

Rhythm and Event Matching (Hypothesis Testing)

The observed sequence of beats and their associated measures is compared against reference data.

The reference data includes patterns derived from a general population database

The reference data may include patterns identified for the subject.

The comparison is based on a set of vectors including measurements of the P-waves, atrial activity and QRST complexes that comprise the sequence of beats.

Implementations

The invention can be implemented in digital electronic circuitry, or in computer hardware, firmware, software, or in combinations thereof. Apparatus of the invention can be implemented in a computer program product tangibly embodied in a machine-readable storage device for execution by a programmable processor. Method actions can be performed by a programmable processor executing a program of instructions to perform functions of the invention by operating on input data and generating output.

The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD_ROM disks. Any of the foregoing can be supplemented by, or incorporated in, ASICs (application-specific integrated circuits).

A number of embodiments of the invention have been described. Nevertheless, it will be understood that various modifications may be made without departing from the spirit and scope of the invention. Accordingly, other embodiments are within the scope of the following claims.

What is claimed is:

1. A system comprises:
   circuitry to receive information from a mobile device including ECG data representative of a beating heart;
   circuitry to analyze the ECG data using at least one pattern to detect a notable finding in the ECG data;
   circuitry to determine at least one additional pattern to send to the mobile device, based on the analysis of the ECG data, with a pattern comprising a specification of characteristics that is used by the mobile device and the circuitry to compare to incoming ECG data during analysis of the incoming ECG data; and
   circuitry to send the at least one determined pattern to the mobile device.

2. The system of claim 1 wherein the determined pattern includes the parameters of a mathematical model.

3. The system of claim 1 wherein the determined pattern includes a template derived from historical ECG data.

4. The system of claim 1 wherein circuitry to analyze the ECG data includes circuitry to compare the analyzed ECG data to templates from categories of cardiac events in order to classify the ECG data.

5. The system of claim 1 wherein sending the determined pattern includes sending software.

6. The system of claim 1 wherein the pattern is a cardiac rhythm pattern.

7. The system of claim 6 wherein the cardiac rhythm pattern is a "bigeminy" rhythm that has alternating normal "N" and ventricular "V" beats, the pattern including a rhythm template that represents the "bigeminy" pattern as eight (8) beats of (N V N V N V N V); and
   wherein incoming beats are compared to the "bigeminy" template to determine if a "bigeminy" condition exists in signals of the incoming beats.

8. The system of claim 1 wherein the pattern is selected based on information from the mobile device, including user characteristics or physiological data samples collected for the user from the mobile device, or data derived by the mobile device from the physiological data samples, including heart beat patterns and heart rhythm patterns.

9. The system of claim 1 wherein the pattern is selected based on user characteristics, including patient clinical and demographic information, and is sent to initialize the mobile device.

10. The system of claim 1 wherein the pattern is new or updated software for execution by the mobile device.

11. The system of claim 1 wherein the pattern comprises a rule that has a set of conditions and an action to perform if the set of conditions is met.

12. The system of claim 11 wherein the rule is a classification rule.

13. The system of claim 11 wherein the rule is a processing rule.

14. The system of claim 11 wherein the rule is a set of rules generated for a specific condition or patient.

15. An arrangement comprises:
   a mobile device for processing ECG data representative of a beating heart, using at least one pattern to detect a notable finding in the ECG data and sending the ECG data corresponding to the notable finding to a second system; and
   the second system executing a process for analyzing the ECG data corresponding to the notable finding and determining at least one new pattern to send to the mobile device, based on the analysis of the ECG data; and
   a process to send the at least one determined pattern to the mobile device.

16. The arrangement of claim 15 wherein the determined pattern includes the parameters of a mathematical model.

17. The arrangement of claim 15 wherein the determined pattern includes a template derived from historical ECG data.

18. The arrangement of claim 15 wherein the process to send the determined pattern sends software to the mobile device.

19. The arrangement of claim 15 wherein the pattern is a cardiac rhythm pattern.

20. The arrangement of claim 15 wherein the pattern is selected based on user characteristics, including patient clinical and demographic information, and is sent to initialize the mobile device.

21. The arrangement of claim 15 wherein the pattern is a rule that has a set of conditions and an action to perform if the set of conditions is met.

22. A method comprises:
   receiving information from a mobile device including ECG data representative of a beating heart;
   analyzing the ECG data using at least one pattern to detect a notable finding in the ECG data;
   determining at least one pattern to send to the mobile device based on analyzing the ECG data; and
   sending the at least one determined pattern to the mobile device.

23. The method of claim 22 wherein the determined pattern includes the parameters of a mathematical model.

24. The method of claim 22 further comprising:
   comparing the analyzed data to templates from categories of cardiac events in order to classify the ECG data.

25. The method of claim 22 wherein the pattern is a rule, the method further comprising:
   generating a rule for a specific condition or patient.

* * * * *